United States Patent [19]

Mitra

[11] Patent Number: 5,648,358
[45] Date of Patent: Jul. 15, 1997

[54] COMPOSITIONS AND METHODS FOR TREATING RESPIRATORY DISORDERS

[76] Inventor: Sekhar Mitra, The Procter & Gamble Company, 8700 Mason-Montgomery Rd., Mason, Ohio 45040

[21] Appl. No.: 611,533

[22] Filed: Mar. 5, 1996

[51] Int. Cl.⁶ .................................................. A61K 31/52
[52] U.S. Cl. .................................................. 514/264
[58] Field of Search ........................................ 514/264

[56] References Cited

U.S. PATENT DOCUMENTS

| | | | |
|---|---|---|---|
| 3,992,541 | 11/1976 | Katz | 424/260 |
| 4,115,589 | 9/1978 | Lednicer | 424/330 |
| 4,134,989 | 1/1979 | Baiocchi et al. | 424/308 |
| 4,292,299 | 9/1981 | Suzuki et al. | 424/16 |
| 4,316,884 | 2/1982 | Alam et al. | 424/19 |
| 4,322,427 | 3/1982 | Buyniski et al. | 424/260 |
| 4,337,255 | 6/1982 | Vogt | 424/251 |
| 4,464,376 | 8/1984 | Sunshine et al. | 424/253 |
| 4,479,956 | 10/1984 | Sunshine et al. | 514/264 |
| 4,486,436 | 12/1984 | Sunshine et al. | 424/253 |
| 4,552,899 | 11/1985 | Sunshine et al. | 514/568 |
| 4,571,400 | 2/1986 | Arnold | 514/282 |
| 4,587,249 | 5/1986 | Sunshine et al. | 514/265 |
| 4,619,934 | 10/1986 | Sunshine et al. | 514/264 |
| 4,656,177 | 4/1987 | Sunshine et al. | 514/420 |
| 4,738,966 | 4/1988 | Sunshine et al. | 514/277 |
| 4,777,174 | 10/1988 | Sunshine et al. | 514/264 |
| 4,783,465 | 11/1988 | Sunshine et al. | 514/255 |
| 4,839,176 | 6/1989 | Pankhania et al. | 424/465 |
| 4,844,907 | 7/1989 | Elger et al. | 424/465 |
| 4,877,620 | 10/1989 | Loew et al. | 424/451 |
| 4,920,149 | 4/1990 | Sunshine et al. | 514/557 |
| 5,164,398 | 11/1992 | Sims et al. | 514/282 |
| 5,478,858 | 12/1995 | Cupps et al. | 514/264 |

FOREIGN PATENT DOCUMENTS

| | | | |
|---|---|---|---|
| 91995 | 1/1982 | European Pat. Off. | A61K 31/215 |
| 88734 | 3/1982 | European Pat. Off. | A61K 31/40 |
| 81823 | 12/1982 | European Pat. Off. | A61K 31/485 |
| 111456 | 12/1982 | European Pat. Off. | A61K 31/495 |
| 388125 | 3/1989 | European Pat. Off. | A61K 31/485 |

OTHER PUBLICATIONS

"Effect of Flurbiprofen, a Cyclooxygenase Inhibiting Drug, on Induced Allergic Rhinitis", *J. Allergy Clin. Immunol.* 1984, pp. 584–589, Brookset al.

Harkness, Drug Interactions Handbook (1984), 82–89.

Harkness, OTC Handbook (1983), 1–17.

The Nurse's 1984–85 Guide to Drug Therapy (1984), 542–543.

Federal Register 41 No. 176, FDA Over-the-Counter Drugs, Establishment of a Monograph for OTC Cold, Cough, Allergy, Bronchodilator and Antiasthmatic Products, Sep. 9, 1976, 38312–88424.

Katsu et al., "Therapeutic effects of Fenbufen on the common cold", Kansenshagaku Zasshi 51(4) (1977), 184–196.

Katsu et al., "Therapeutic Utility of Naproxen on Acute Respiratory Infection" Kansenshagaku Zasshi 52(5) (1978), 148–163.

Fujimori et al., "Clinical Evaluation of Clinoril Tablets in Acute Upper Respiratory Tract Infections", Kansensho-shi 56(12) (1982), 1186–1195.

Katsu et al., :"Double–blind Central Study of Miroprofen in Acute Upper Respiratory Tract Infections—Comparison with Ibuprofen", Kansenshagaku Zasshi 50(5) (1982), 435–453.

Katsu et al., "Clinical Evaluation of Sulindac (Clinoril) in the Treatment of Acute Upper Respiratory Tract Inflammation—Double Blind Comparison with Ibuprofen", Kansenshagaku Zasshi 57(3) (1983), 260–272.

*Primary Examiner*—James H. Reamer
*Attorney, Agent, or Firm*—Douglas C. Mohl; Mary Catherine Poland; Jacobus C. Rasser

[57] ABSTRACT

The present invention relates to compositions and methods for providing improved treatment, management or mitigation of cold, cold-like, allergy, sinus and/or flu symptoms by administering a safe and effective amount of a composition comprising caffeine and certain pyrrolidine and piperidine ether antihistaminic agents.

15 Claims, No Drawings

COMPOSITIONS AND METHODS FOR TREATING RESPIRATORY DISORDERS

TECHNICAL FIELD

The present invention relates to compositions and methods for providing improved treatment, management or mitigation of cold, cold-like, allergy, sinus and/or flu symptoms by administering a safe and effective amount of a composition comprising caffeine and certain pyrrolidine and piperidine ether antihistaminic agents.

BACKGROUND OF THE INVENTION

The common cold, although not usually a serious illness, is a highly prevalent, discomforting and annoying affliction. The term "common cold" is applied to minor respiratory illnesses caused by a variety of different respiratory viruses. While rhinoviruses are the major known cause of common colds, accounting for approximately 30 percent of colds in adults, viruses in several other groups are also important. While immune responses occur, and infection with some respiratory tract viruses therefore could be prevented by a vaccine, development of a polytypic vaccine to cover all possible agents is impractical. Thus, the problem of controlling acute upper respiratory disease presents complex challenges, and the long-desired discovery of a single cure for the common cold is an unrealistic expectation.

Early symptoms may be minimal with only mild malaise, sore throat and nasal complaints. With rhinovirus infection, symptoms of nasal discharge, nasal congestion, and sneezing usually commence on the first day of illness and progress to maximum severity by the second or third day. Along with nasal symptoms may come sore, dry or scratchy throat and hoarseness and cough. Other symptoms may include mild burning of the eyes, loss of smell and taste, a feeling of pressure or fullness in the sinuses or ears, headache, and vocal impairment. Fever can occur, but is uncommon. Influenza infection generally includes fever, often of sudden onset and persisting for several days, and with great severity; generalized aches and pains; fatigue and weakness; and chest discomfort.

At present, only symptomatic treatment is available for the common cold. The costs of treating colds with over-the-counter medications in the United States is estimated at an annual cost of over 1.5 billion dollars. The direct costs of treatment in outpatient clinics is estimated at almost four billion dollars. Indirect costs, based on the amount of loss in wages because of restricted activity are substantially higher.

Exemplary prior art formulations for treatment of cough, cold, cold-like, allergy, sinus and/or flu symptoms and the discomfort, pain, fever and general malaise associated therewith generally contain an analgesic (aspirin or acetaminophen) and one or more antihistaminics, decongestants, cough suppressants, antitussives and expectorants.

The present inventors have found that selected compositions comprising caffeine along with certain pyrrolidine and piperidine ether antihistaminic agents provides improved treatment, management or mitigation of cold, cold-like, allergy, sinus and/or flu symptoms, including nasal congestion.

It is therefore an object of the present invention to provide a method for the treatment of cough, cold, cold-like, allergy, sinus and/or flu symptoms in a mammalian organism in need of such treatment comprising administering to such organism the compositions of the present invention. Such symptoms as used herein refer to coryza, nasal congestion, sinus congestion, sinus pain, upper respiratory infections, otitis, sinusitis, etc.

SUMMARY OF THE INVENTION

The present invention relates to compositions and methods for providing improved treatment, management or mitigation of cold, cold-like, allergy, sinus and/or flu symptoms by administering a safe and effective amount of a composition comprising caffeine and certain pyrrolidine and piperidine ether antihistaminic agents.

All percentages and ratios used herein are by weight and all measurements are made at 25° C. unless otherwise specified.

DETAILED DESCRIPTION OF THE INVENTION

The present invention relates to compositions and methods for providing improved treatment, management or mitigation of cold, cold-like, allergy, sinus and/or flu symptoms by administering a safe and effective amount of a composition comprising caffeine and certain pyrrolidine and piperidine ethers.

Pyrrolidine and piperidine ether antihistaminic agents

The pyrrolidine and piperidine ethers are of the formula:

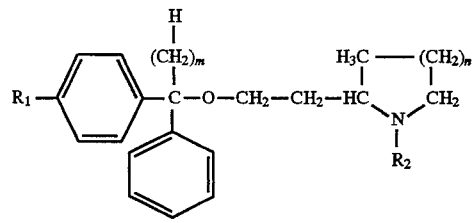

wherein $R_1$ is a radical selected from the group consisting of hydrogen, halogen, lower alkyl containing from 1 to 4 carbon atoms and lower alkoxy containing from 1 to 4 carbon atoms, $R_2$ is a radical selected from the group consisting of lower alkyl containing 1 to 4 carbon atoms, m is an integer from 0, 1, 2 and 3 and n is an integer from 1 to 2, with the proviso that m+n must be at least 2. Salts of these compounds are also useful.

These compounds have antihistamine properties and are more fully described in U.S. Pat. No. 3,097,212 to Jucker et al., issued Jul. 9, 1963, incorporated by reference herein.

Preferred for use herein are N-methyl-2-[2'(α-methyl-p-chloro-benzhydryl-oxy)ethyl]-pyrrolidine and N-methyl-2-[2'(α-methyl-p-bromo-benzhydryl-oxy)ethyl]-pyrrolidine. Most preferred for use herein is N-methyl-2-[2'(α-methyl-p-chloro-benzhydryl-oxy)ethyl]-pyrrolidine which is commonly known as clemastine fumarate and sold as Tavist® by Sandoz Pharmaceuticals.

The safe and effective amount of these pyrrolidine and piperidine ethers generally ranges from about 0.1 to about 10 mg, preferably from about 0.3 to about 3 mg, more preferably from about 0.5 to about 2 mg and most preferably from about 0.67 to about 1.34 mg.

Caffeine

An additional agent found useful in the present compositions is caffeine. Caffeine has been found to lessen the sedating effect of the pyrrolidine and piperidine ethers. The level of caffeine use is generally from about 20 mg to about 500 mg, preferably from about 50 mg to about 200 mg, most preferably from about 65 mg to about 100 mg.

Additional Pharmaceutical Actives

The compositions of the present invention can also include at least one other pharmacological active selected from the following class: (a) a decongestant, (b) an expectorant (c) an additional antihistamine and (d) an antitussive. The decongestants useful in the compositions of the present invention include pseudoephedrine, phenylpropanolamine, phenylephrine and ephedrine, their pharmaceutically acceptable salts, and mixtures thereof. The antitussives useful in the present invention include those such as dextromethorphan, chlophedianol, carbetapentane, caramiphen, noscapine, diphenhydramine, codeine, hydrocodone, hydromorphone, fominoben, their pharmaceutically-acceptable salts, and mixtures thereof. The additional antihistamines useful in the present invention include those such as chlorpheniramine, brompheniramine, dexchlorpheniramine, dexbromphreniramine, triprolidine, azatadine, doxylamine, tripelennamine, cyproheptadine, hydroxyzine, carbinoxamine, phenindamine, bromodiphenhydramine, pyrilamine, their pharmaceutically acceptable salts, as well as the non-sedating antihistamines which include acrivastine, AHR-11325, astemizole, azatadine, azelastine, cetirizine, ebastine, ketotifen, lodoxamide, loratidine, levocabastine, mequitazine, oxatomide, setastine, tazifylline, temelastine, and terfenadine, their pharmaceutically acceptable salts and mixtures thereof. The expectorants (also known as mucolytic agents) useful in the present invention include glyceryl guaiacolate, terpin hydrate, ammonium chloride, N-acetylcysteine and bromhexine, ambroxol, their pharmaceutically acceptable salts, and mixtures thereof. All of these components, as well as their acceptable dosage ranges are described in the following: U.S. Pat. No. 4,783,465 to Sunshine et al., issued Nov. 8, 1988, U.S. Pat. No. 4,619,934 to Sunshine et al., issued Oct. 28, 1986, which are incorporated by reference herein. Additional agents which are found useful in the present compositions are $\alpha$-agonists such as those disclosed in U.S. Pat. 5,478,858, issued Dec. 26, 1995, incorporated herein by reference in its entirety.

Various oral dosage forms can be used, including such solid forms as tablets, caplets, capsules, granules, lozenges and bulk powders and liquid forms such as syrups and suspensions. Controlled release dosage forms which provide a controlled release of these active(s) are also useful. These oral forms comprise a safe and effective amount, usually at least about 5% of the active components. Solid oral dosage forms preferably contain from about 5% to about 95%, more preferably from about 10% to about 95%, and most preferably from about 25% to about 95% of the active components. Liquid oral dosage forms preferably contain from about 1% to about 50% and more preferably from about 1% to about 25% and most preferably from about 3% to about 10% of the active components.

Tablets can be compressed, triturated, enteric-coated, sugar-coated, film-coated or multiple compressed, containing suitable binders, lubricants, diluents, disintegrating agents, coloring agents, flavoring agents, preservatives and flow-inducing agents. Also useful are soft gelatin capsules.

Liquid oral dosage forms include aqueous and nonaqueous solutions, emulsions, pseudo emulsions, suspensions, and solutions and/or suspensions reconstituted from non-effervescent granules, containing suitable solvents, preservatives, emulsifying agents, suspending agents, diluents, sweeteners, taste-masking agents, coloring agents, and flavoring agents. Specific examples of pharmaceutically acceptable carriers and excipients that may be used to formulate oral dosage forms, are described in U.S. Pat. No. 3,903,297, Robert, issued Sep. 2, 1975, incorporated by reference herein. Techniques and compositions for making solid oral dosage forms are described in Marshall, "Solid Oral Dosage Forms," *Modern Pharmaceutics*, Vol. 7, (Banker and Rhodes, editors), 359–427 (1979), incorporated by reference herein. Techniques and compositions for making tablets (compressed and molded), capsules (hard and soft gelatin) and pills are described in *Remington's Pharmaceutical Sciences* (Arthur Osol, editor), 1553–1593 (1980), incorporated herein by reference.

In preparing the liquid oral dosage forms, the active component is incorporated into an aqueous-based orally acceptable pharmaceutical carrier consistent with conventional pharmaceutical practices. An "aqueous-based orally acceptable pharmaceutical carder" is one wherein the entire or predominant solvent content is water. Typical carders include simple aqueous solutions, syrups, dispersions and suspensions, and aqueous based emulsions such as the oil-in-water type. The most preferred carrier is a suspension of the pharmaceutical composition in an aqueous vehicle containing a suitable suspending agent. Suitable suspending agents include Avicel RC-591 (a microcrystalline-cellulose/sodium carboxymethyl cellulose mixture available from FMC), guar gum and the like. Such suspending agents are well known to those skilled in the art. While the amount of water in the compositions of this invention can vary over quite a wide range depending upon the total weight and volume of the active component and other optional non-active ingredients, the total water content, based on the weight of the final composition, will generally range from about 20 to about 75%, and, preferably, from about 20 to about 40%, by weight/volume.

Although water itself may make up the entire carrier, typical liquid formulations preferably contain a co-solvent, for example, propylene glycol, glycerin, sorbitol solution and the like, to assist solubilization and incorporation of water-insoluble ingredients, such as flavoring oils and the like into the composition. In general, therefore, the compositions of this invention preferably contain from about 5 to about 25 volume/volume percent and, most preferably, from about 10 to about 25 volume/volume percent, of the co-solvent.

Other optional ingredients well known to the pharmacist's art may also be included in amounts generally known for these ingredients, for example, natural or artificial sweeteners, flavoring agents, colorants and the like to provide a palatable and pleasant looking final product, antioxidants, for example, butylated hydroxy anisole or butylated hydroxy toluene, and preservatives, for example, methyl or propyl paraben or sodium benzoate, to prolong and enhance shelf life. A highly preferred optional component is caffeine.

METHOD OF TREATMENT

The amount of the pharmaceutical composition administered depends upon the percent of active ingredients within its formula, which is a function of the amount of the naphthalene derivative and any optional components such as a decongestant, cough suppressant, expectorant and/or antihistamine required per dose, stability, release characteristics and other pharmaceutical parameters.

Usually from about 1 mg/kg to about 50 mg/kg per day, preferably from about 2 mg/kg to about 30 mg/kg per day and most preferably from about 3 mg/kg per day to about 20 mg/kg per day of the pharmaceutical composition is administered as described herein. This amount can be given in a single dose, or, preferably, in multiple (two to six) doses repeatedly or sustained release dosages over the course of treatment. Generally, each individual dosage of the pharmaceutical composition of the present invention range from about 1 mg/kg to about 25 m/kg, preferably from about 2 mg/kg to about 15 mg/kg and most preferably from about 3 mg/kg to about 10 mg/kg. While dosages higher than the foregoing are effective to provide relief from cough, cold-like, flu, flu-like and allergic rhinitis symptoms, care must be taken, as with any drug, in some individuals to prevent adverse side effects.

The following examples illustrate embodiments of the subject invention wherein both essential and optional ingredients are combined.

EXAMPLE I

A hard gelatin capsule composition for oral administration is prepared by combining the following ingredients:

| Ingredient | Amount |
|---|---|
| Caffeine | 100.00 mg |
| Clemastine fumarate | 0.67 mg |
| Pseudoephedrine HCl | 30.00 mg |

Triturate active ingredients and q.s. with lactose to selected capsule size.

Administration of one or two the above capsules every four to twelve hours to a human in need of treatment provides improved relief from cough, cold-like, flu, flu-like and allergic rhinitis symptoms.

EXAMPLE II

A hard compressed caplet composition for oral administration is prepared by combining the following ingredients:

| Ingredient | Amount |
|---|---|
| Caffeine | 100.00 mg |
| Clemastine fumarate | 0.67 mg |
| Hydroxypropyl methylcellulose | 300.00 mg |
| Corn starch | 150.00 mg |
| Pregelatinized starch | 40.00 mg |
| Silicon dioxide, colloidal | 1.50 mg |
| Stearic acid TP fine powder | 2.00 mg |
| Sodium lauryl sulfate | 0.50 mg |

Administration of two caplets every twelve hours to a human in need of treatment provides improved relief from cough, cold-like, flu-like and allergic rhinitis symptoms.

EXAMPLE III

A hard compressed tablet composition for oral administration is prepared by combining the following ingredients:

| Ingredient | Amount |
|---|---|
| Caffeine | 100.00 mg |
| Clemastine fumarate | 1.34 mg |
| Magnesium stearate | 2.00 mg |
| Povidone | 10.00 mg |
| Talc | 12.00 mg |
| Microcrystalline cellulose | 45.00 mg |

Administration of one of the above tablets every twelve hours to a human in need of treatment provides improved relief from cough, cold-like, flu, flu-like and allergic rhinitis symptoms.

EXAMPLE IV

A liquid composition for oral administration is prepared by combining the following ingredients:

| Ingredient | % W/V |
|---|---|
| Caffeine | 100.00 mg |
| Alcohol (95%) | 25.0000 |
| Clemastine fumarate | 0.0134 |
| Propylene Glycol | 25.0000 |
| Sodium Citrate | 2.0000 |
| Citric Acid | 0.2500 |
| Liquid Sugar (Simple Syrup) | 25.0000 |
| Glycerin | 7.0000 |
| Colorants | 0.0080 |
| Flavor | 0.5000 |
| Water, Purified QS | 100.0000 |

The purified water (approximately 10% of the final batch volume) is poured into a batch container equipped with a lightnin' mixer. The sodium citrate, citric acid, and actives other than naproxen sodium are added sequentially and dissolved with agitation. The glycerin and liquid sugar are then added. In a separate container the colorants are added to purified water (approximately 0.5% of the final batch volume). This colorant solution is then added to the first batch container. In a separate container the naproxen sodium is added to the alcohol while stirring. The propylene glycol and flavors are added to this alcohol premix and the resulting mixture is stirred until homogeneous and then added to the first container. The remaining purified water is added to the resulting mixture and stirred.

Administration of 10 ml to 20 ml (2 to 4 teaspoonsful) every twelve hours to a human in need of treatment provides improved relief from cough, cold-like, flu, flu-like and allergic rhinitis symptoms.

EXAMPLE V

A liquid composition for oral administration is prepared by combining the following ingredients:

| Ingredient | % W/V |
|---|---|
| Caffeine | 100.00 mg |
| Clemastine fumarate | 0.0067 |
| Alcohol (95%) | 25.0000 |
| Propylene Glycol | 25.0000 |
| Sodium Citrate | 2.0000 |
| Citric Acid | 0.2500 |
| Liquid Sugar (Simple Syrup) | 25.0000 |
| Glycerin | 7.0000 |
| Colorants | 0.0080 |
| Flavor | 0.5000 |
| Water, Purified QS | 100.0000 |

The purified water (approximately 10% of the final batch volume) is poured into a batch container equipped with a lightnin' mixer. The sodium citrate, citric acid, clemastine fumarate are added sequentially and dissolved with agitation. The glycerin and liquid sugar are then added. In a separate container the colorants are added to purified water (approximately 0.5% of the final batch volume). This colorant solution is then added to the first batch container. In a separate container the ibuprofen is added to the alcohol while stirring. The propylene glycol and flavors are added to this alcohol premix and the resulting mixture is stirred until homogeneous and then added to the first container. The remaining purified water is added to the resulting mixture and stirred.

Administration of 10 ml to 20 ml (2 to 4 teaspoonsful) every four to twelve hours to a human in need of treatment provides improved relief from cough, cold-like, flu, flu-like and allergic rhinitis symptoms.

EXAMPLE VI

A liquid composition for oral administration is prepared by combining the following ingredients:

| Ingredient | % W/V |
|---|---|
| Caffeine | 100.00 mg |
| Clemastine fumarate | 0.009 |
| Dextromethorphan HBr | 0.300 |
| Alcohol (95%) | 25.000 |
| Propylene Glycol | 25.000 |
| Sodium Citrate | 2.000 |
| Citric Acid | 0.250 |
| Liquid Sugar (Simple Syrup) | 25.000 |
| Glycerin | 7.000 |
| Colorants | 0.008 |
| Flavor | 0.500 |
| Water, Purified QS | 100.000 |

The purified water (approximately 10% of the final batch volume) is poured into a batch container equipped with a lightnin' mixer. The sodium titrate, citric acid and clemastine fumarate are added sequentially and dissolved with agitation. The glycerin and liquid sugar are then added. In a separate container the colorants are added to purified water (approximately 0.5% of the final batch volume). This colorant solution is then added to the first batch container. In a separate container the S (+) ibuprofen lysinate and dextromethorphan HBr are added sequentially to the alcohol while stirring.

The propylene glycol and flavors are added to this alcohol premix and the resulting mixture is stirred until homogeneous and then added to the first container. The remaining purified water is added to the resulting mixture and stirred.

Administration of 20 ml (4 teaspoonsful) every eight to twelve hours to a human in need of treatment provides improved relief from cough, cold-like, flu, flu-like and allergic rhinitis symptoms.

What is claimed is:

1. A composition for providing improved treatment, management or mitigation of cold, cold-like, allergy, sinus and/or flu symptoms by administering a safe and effective amount of a composition comprising:
   (a) caffeine; and
   (b) a pyrrolidine or piperidine ether antihistaminic agent of the formula:

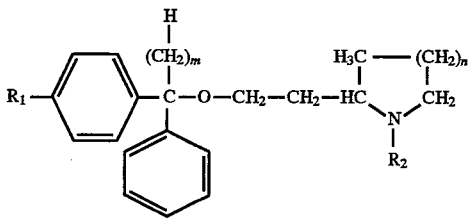

wherein $R_1$ is a radical selected from the group consisting of hydrogen, halogen, lower alkyl containing from 1 to 4 carbon atoms and lower alkoxy containing from 1 to 4 carbon atoms, $R_2$ is a radical selected from the group consisting of lower alkyl containing 1 to 4 carbon atoms, m is an integer from 0, 1, 2 and 3 and n is an integer from 1 to 2, with the proviso that m+n must be at least 2.

2. A pharmaceutical composition according to claim 1 wherein said antihistaminic agent is selected from the group consisting of N-methyl-2-[2'(α-methyl-p-chloro-benzhydryl-oxy)ethyl]-pyrrolidine and N-methyl-2-[2'(α-methyl-p-bromo-benzhydryl-oxy)ethyl]-pyrrolidine and salts thereof.

3. A pharmaceutical composition according to claim 2 which in addition contains a propionic acid derivative selected from the group consisting of ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofen.

4. A pharmaceutical composition according to claim 1 wherein said antihistaminic agent is N-methyl-2-[2-(α-methyl-p-chloro-benzhydryl-oxy)ethyl]-pyrrolidine.

5. A pharmaceutical composition according to claim 3 which also contains an additional pharmaceutical active selected from the group consisting of decongestants, expectorants, additional antihistamines and antitussives.

6. A pharmaceutical composition according to claim 5 wherein said decongestant is pseudoephedrine, phenylpropanolamine, phenylephrine and ephedrine, mixtures thereof or pharmaceutically acceptable salts thereof.

7. A pharmaceutical composition according to claim 5 wherein said antitussive is selected from the group consisting of dextromethorphan, chlophedianol, carbetapentane, caramiphen, noscapine, diphenhydramine, codeine, hydrocodone, hydromorphone, fominoben, mixtures thereof or pharmaceutically acceptable salts thereof.

8. A pharmaceutical composition according to claim 5 wherein said expectorant is an expectorant or mucolytic such as glyceryl guaiacolate, terpin hydrate, ammonium chloride, N-acetylcysteine, bromhexine and ambroxol, mixtures thereof or pharmaceutically acceptable salts thereof.

9. A pharmaceutical composition according to claim 5 wherein said additional antihistamine is selected from the group consisting of chlorpheniramine, brompheniramine, dexchlorpheniramine, dexbromphreniramine, triprolidine, doxylamine, tripelennamine, cyproheptadine, carbinoxamine, bromodiphenhydramine, pyrilamine, acrivastine, AHR-11325, phenindamine, astemizole, azatadine, azelastine, cetirizine, ebastine, ketotifen, lodoxamide, loratidine, levocabastine, mequitazine, oxatomide, setastine, tazifylline, temelastine, and terfenadine, mixtures thereof or pharmaceutically acceptable salts thereof.

10. A pharmaceutical composition according to claim 1 which in addition contains an α-agonist compound.

11. A method for the treatment of cough, cold, cold-like and/or flu symptoms in a mammalian organism in need of such treatment comprising administering to such organism the composition of claim 1.

12. A method for the treatment of nasal congestion in a mammalian organism in need of such treatment comprising administering to such organism the composition of claim 1.

13. A method for the treatment of sinus pressure, pain and/or drainage in a mammalian organism in need of such treatment comprising administering to such organism the composition of claim 1.

14. A method for the treatment of nasal congestion in a mammalian organism in need of such treatment comprising administering to such organism the composition of claim 6.

15. A method for the treatment of nasal congestion in a mammalian organism in need of such treatment comprising administering to such organism the composition of claim 7.

* * * * *